United States Patent [19]

Ritze

[11] 4,129,638
[45] Dec. 12, 1978

[54] COMPOSITIONS OF MATTER FOR COLORING TOOTHPASTE AND METHOD OF PREPARING SAME

[75] Inventor: Lyle W. Ritze, Hamilton Township, Warren County, Ohio

[73] Assignee: The Procter & Gamble Company, Cincinnati, Ohio

[21] Appl. No.: 744,078

[22] Filed: Nov. 22, 1976

Related U.S. Application Data

[60] Continuation of Ser. No. 507,636, Sep. 20, 1974, abandoned, which is a division of Ser. No. 837,303, Jun. 27, 1969, abandoned.

[51] Int. Cl.² ............................................. B29B 1/02
[52] U.S. Cl. ................................ 264/117; 106/309; 260/28 R; 260/28.5 R; 264/118; 264/140
[58] Field of Search ............... 264/140, 118, 117, 77, 264/73, 349, 211; 260/28 R, 28.5 R; 106/272, 309, 308 Q

[56] References Cited

U.S. PATENT DOCUMENTS

| | | | |
|---|---|---|---|
| 2,119,189 | 5/1938 | Widmer | 260/39 P |
| 2,512,459 | 6/1950 | Hamilton | 260/28.5 A |
| 2,597,467 | 5/1952 | Fisher et al. | 260/39 P |
| 2,772,982 | 12/1956 | Vesce | 424/49 |
| 3,070,510 | 12/1962 | Cooley et al. | 424/49 |
| 3,095,400 | 6/1963 | Martino et al. | 260/43 |
| 3,251,800 | 5/1966 | Cooley et al. | 424/49 |
| 3,357,951 | 12/1967 | Adams | 424/49 |
| 3,574,823 | 4/1971 | Roberts et al. | 424/49 |
| 3,584,114 | 6/1971 | Cavalli et al. | 264/117 |
| 3,778,288 | 12/1973 | Ridge et al. | 106/309 |

FOREIGN PATENT DOCUMENTS

| | | |
|---|---|---|
| 1265702 | 4/1968 | Fed. Rep. of Germany. |
| 1535547 | 7/1968 | France. |
| 1558959 | 1/1969 | France. |
| 626695 | 7/1949 | United Kingdom. |
| 660137 | 10/1951 | United Kingdom. |

OTHER PUBLICATIONS

Soap and Chem. Spec.,-Patton, 12-1957.
Pigment-Herstellung Eigenschaften, Andendung-Kittel-p. 90, 1960.
Encyclopadie der Technischen Chemie, 3rd Ed., vol. 1, pp. 731-736, Ullman, 1951.

*Primary Examiner*—Jeffery R. Thurlow
*Attorney, Agent, or Firm*—Douglas C. Mohl; Ronald L. Hemingway; Richard C. Witte

[57] ABSTRACT

Toothpaste compositions containing wax or gel agglomerates of nontoxic pigment particles and a process for preparing such agglomerates by dispersing pigment particles in a molten wax, solidifying the wax dispersion by cooling same, and reducing the resulting agglomerates to a desired particle size. The agglomerates of colored particles serve to impart a distinctive and pleasing appearance to toothpaste compositions.

5 Claims, No Drawings

COMPOSITIONS OF MATTER FOR COLORING TOOTHPASTE AND METHOD OF PREPARING SAME

CROSS-REFERENCE TO RELATED APPLICATION

This is a continuation, of application Ser. No. 507,636, filed Sept. 20, 1974 now abandoned, which is a divisional application of the abandoned application of Lyle W. Ritze and Robert A. Catlin, Ser. No. 837,303, filed June 27, 1969, entitled "COMPOSITIONS OF MATTER FOR COLORING TOOTHPASTE".

BACKGROUND OF THE INVENTION

This invention relates to speckled toothpastes containing agglomerated pigment particles. More specifically this invention relates to toothpastes colored in a speckled fashion with agglomerates of water-insoluble non-toxic pigment particles and a process for preparing said agglomerates.

Color has been acknowledged to play an important role in consumer acceptance of many products. In many cases color has been used to distinguish particular products in the market place and to identify products having particular distinct properties. Colored products are usually formulated by merely adding the desired dye to the other components prior to the mixing stage of the process. As the dyes currently utilized in toothpaste are all water-soluble, and varying large amounts of water are present in toothpaste, the desired color spreads and uniformly colors the entire product. An alternative means of uniformly coloring a toothpaste is to disperse uniformly in the paste very small particles of insoluble colored material which acts as a pigment. Although this material is discerned as discrete colored particles when the paste is examined under a magnifying lens, to the naked eye the paste has a uniform colored appearance. For example, colored thermosetting cross-linked resin particles can be used for uniform pigmentation of toothpastes as is disclosed in the abandoned U.S. patent application of R. A. Shaffer, Ser. No. 165,585, filed June 23, 1971, which is a continuation of Ser. No. 837,358, filed June 27, 1969, now abandoned.

Although overall colored effects as described above can be quite pleasing to the consumer, one of the most attractive and effective uses of color is a speckled effect which can be achieved by incorporating a minor proportion of particles which are large enough to be readily discernible with the naked eye into a composition of contrasting color. By uniformly dispersing such colored particles, a product having numerous, discrete, well-defined centers of contrasting color or colors randomly but uniformly distributed therethrough, i.e., a speckled product, is attained which presents a striking and highly distinctive appearance. While speckled toothpastes have long been known, the speckling is achieved by such substances as gold leaf and charcoal which are not really satisfactory from an aesthetic or economic standpoint. Thus, while the concept of speckling a toothpaste is old per se, no really effective means for executing this concept has been provided in the prior art.

The main requirements of such a speckle is that it be of sufficient size to be discernible as such; that it maintain its integrity and distinctness in the toothpaste base until the product is used; and that it be sufficiently frangible to break up into small particles in use. Thus, it must not leach, i.e., bleed, and color the entire dentifrice. Since the dyes certified for use in dentifrice products by the U.S. Food and Drug Administration are all water-soluble and toothpastes generally contain sufficient quantitites of water to cause the dyes to leach and color the entire product, it has not been possible to prepare speckles which are colorfast yet sufficiently frangible to disintegrate in use so that they are not detectable in the mouth. Solid particles of the size required to produce the speckled effect generally produce an unpleasant gritty "berry seed" sensation in use, and actually become lodged between the teeth unless they break up into smaller particles when brushed upon the teeth.

SUMMARY OF THE INVENTION

In general terms this invention is a speckled toothpaste composition comprising a toothpaste base having uniformly dispersed therein agglomerates of pigment particles having a color contrasting to that of said toothpaste base, said particles having a mean particle size of less than 420 microns and consisting of a water-insoluble nontoxic, colorfast, relatively inert substance, and being agglomerated to a mean particle size within the range from about 200 to about 500 microns with a wax or gel as hereinafter defined.

In its process aspect, the invention is a process for preparing agglomerates of pigment particles which comprises (1) melting a wax having a hardness value of from about 0 to 65; (2) uniformly dispersing pigment particles in the molten wax; (3) cooling the wax dispersion of pigment particles to solidification; and (4) reducing the solid wax dispersion to a mean particle size within the range from about 200 to about 500 microns.

It is thus an object of the present invention to provide toothpaste compositions which are colored in a speckled manner by agglomerates of pigment particles.

It is a further object of the present invention to provide novel agglomerates of pigment particles and processes for preparing them.

These and other objects are achieved in the practice of the present invention as will become apparent from the following detailed description of the invention.

DETAILED DESCRIPTION OF THE INVENTION

Pigment particles which can be used to prepare agglomerates useful for speckling toothpaste in accordance with this invention are essentially color-fast, nontoxic, and water-insoluble. The color of the pigment particles should be of a character that the agglomerates formed therefrom are readily distinguishable from the toothpaste base.

The primary attributes of color are (a) hue, (b) brightness or value, and (c) saturation, purity or chroma. The hue of the particles is a matter of choice, and the preferred hue depends on the color of the toothpaste base (a contrasting hue being necessary to secure a speckled appearance); however, using the Munsell system of color notation (see the Munsell Book of Color, Munsell Color Co., Inc., Baltimore, Maryland, 1929), the particle preferably has a Munsell Value of from 4 to 7, and a Munsell Chroma of more than 4.

The pigment particles must be essentially color-fast, i.e., must not leach a significant amount of color in the presence of water. Thus, water-soluble dyes per se cannot be used in the practice of this invention. Water-soluble dyes can be used to prepare pigment particles which will not leach color, however. Color-fast dyed thermosetting resin particles and their preparation are disclosed in the Shaffer application cited hereinbefore and such particles are preferred for use herein. Other pigment particles which can be used to prepare colored agglomerates include, for example, non-toxic water-insoluble, inorganic pigments such as chromium oxide greens, carbon blacks, ultramarine blues and pinks, and ferric oxides; dyed cellulose particles such as dyed cotton linters and dyed wood pulp; and water-insoluble dye lakes prepared by extending calcium or aluminum salts of FD&C water-soluble dyes on alumina, such as FD&C Green #1 lake, FD&C Blue #2 lake and FD&C Yellow #5 lake.

The mean particle size of the pigment particle can range from about 5 to about 490 microns, and preferably from 10 to about 200 microns. Larger particles tend to feel gritty in the mouth and stick between the teeth. The particle sizes referred to herein can be determined for example by microscopic measurements using a calibrated eyepiece.

The pigment particles can comprise from about 10% to about 90% by weight of the total agglomerate. Preferably, the pigment is used at a concentration in the range from about 30% to about 50% by weight of the total agglomerate. Pigment particles having lower Munsell Value and Chroma are preferably employed at higher concentrations.

The agglomerating agents which can be used in the practice of this invention include waxes and gelling agents. Suitable waxes are those which are non-toxic and have a hardness value of from about 0 to about 65 (ASTM Test D 1321-65) and preferably from about 0 to 5. Examples of suitable waxes include carnauba wax, candelilla wax, purified montan wax, castor wax, paraffin, ceresin wax and bayberry wax. Preferred waxes have a melting point above 70° F., more preferably from 180° to 230° F. Additional waxes having these properties which can be used herein are disclosed in Soap & Chem. Specialties, Vol. 33, page 141 (1957). See also Industrial Waxes, Vol. I and II, H. Bennett, Chemical Publishing Co., Inc., New York, 1963, for a discussion of waxes and their properties.

Suitable gelling agents are those that form stable, firm gels which are: non-toxic; hard enough to withstand conventional shear stresses when admixed in the dentifrice or extruded from the toothpaste tube; frangible enough to disintegrate into smaller particles at time of use to give no adverse mouth impression; light colored; innocuous in flavor and odor; and compatible with toothpaste ingredients. Gelling agents which can be used to form agglomerates of pigment particles include agar-agar, cassava starch, Avicel (microcrystalline cellulose supplied by FMC Corp.), and high molecular weight carboxyvinyl polymers such as Carbopol 940, supplied by the B. F. Goodrich Chemical Company.

The wax or gelling agent can comprise from 10% to 90% by weight of the total agglomerate. Preferably, this component of the agglomerate is used in concentrations ranging from about 50% to about 70% by weight of the total agglomerate.

As hereinbefore stated, the final agglomerate can have a mean particle size within the range from about 200 to about 500 microns. Agglomerates having a mean particle size of less than about 200 microns are not clearly visible as distinct speckles. Preferred agglomerates have a mean particle size of approximately 300 microns.

In a preferred embodiment of this invention agglomerates of pigment particles are prepared by a process which comprises the steps of (1) melting from about 50 to about 70 parts by weight of a wax having a hardness value of from 0 to 5; (2) uniformly dispersing from about 30 to about 50 parts by weight of pigment particles in the molten wax: (3) cooling the wax dispersion of pigment particles to solidification and (4) reducing the solid wax dispersion to a mean particle size within the range from about 200 to about 500 microns.

The wax is first heated to a temperature above its melting point in a vessel equipped with mixing apparatus. The preferred waxes for the purpose of this process have melting points within the range from about 180° to about 230° F. It is essential that the wax be maintained at its melting point temperature or above when the pigment particles are added. The maximum temperature is not critical; however, it should not be so high that decomposition occurs or a fire hazard is presented.

The pigment particles are added to the molten wax in increments which are sufficiently small to avoid a temperature drop below the melting point of the wax. Thorough mixing of the particles in the wax in molten state is necessary to assure complete dispersion and coating of the pigment particles with wax and proper agglomeration.

After uniform dispersion of the pigment particles in the molten wax has been achieved, it is generally desirable to cool and solidify the dispersion using means which produce an easily handled solid such as by applying the molten dispersion to a drum flaker, pouring the dispersion in thin layers upon cooling trays from which the solid can be removed as flakes, or by admixing the dispersion in water and cooling same. Any method of solidifying the dispersion which yields the final agglomerates or larger pieces suitable for reduction to the final agglomerate can be used. Conventional methods suitable for this process step are described in Chapter 11 of the Chemical Engineer's Handbook, John H. Perry, 4th Ed., McGraw Hill Book Co., N.Y. 1963, under the heading "Indirect Heat Transfer Equipment for Solids". Preferably, the solid dispersion is solidified to the desired size by flaking on a drum flaker.

Reduction of the solid wax dispersion to agglomerates of a desired size can be accomplished by conventional size reduction techniques described in Chapter 8, Perry's Chemical Engineering Handbook. Preferably, reduction is accomplished by a hammer mill.

It is generally desirable to screen the agglomerates after the reduction step to recover the agglomerates of the desired size (200 to 500 microns). Size classification in this manner can be accomplished by conventional techniques and equipment such as the double screen Tyler-Hummer Vibrating Sifter. The agglomerates which are greater than 500 microns can be reground and the smaller agglomerates can be remelted, solidified and ground to the desired size range.

The preparation and utilization of colored particle agglomerates in accordance with the invention is shown by the following examples which are presented for purposes of illustration only and are not intended to limit the invention.

EXAMPLE I

Agglomerates of green thermosetting resins suitable for speckling a toothpaste were prepared as follows:

65 parts of carnauba wax were heated to a temperature of 230° F. in a melt tank equipped with a flat blade turbine agitator. 35 parts of green thermosetting urea-formaldehyde resin particles (prepared in accordance with Example I of the Shaffer application hereinbefore cited) were added to the molten wax with constant agitation. The particles were thoroughly dispersed in the wax and the wax dispersion was then distributed upon a drum flaker. After solidification, the flakes were pulverized in a micro-pulverizer hammer mill, and the resulting agglomerates were screened in a Tyler-Hummer Vibrating Sifter to recover those having a particle size in the range from 200 to 500 microns. The agglomerates had a Munsell Value of from 4 to 7 and a Munsell Chroma greater than 4.

Similar agglomerates are secured when paraffin, ceresin wax or castor wax are used in place of carnauba wax in the foregoing process. The green urea-formaldehyde resin can be replaced by particles of dyed cellulose, chromium oxide green, FD&C Blue #2 dye lake or ultramarine blue with comparable results.

EXAMPLE II

Blue paraffin agglomerates of a dye lake were prepared in accordance with this invention as follows:

To 140 parts of molten paraffin were added 60 parts of washed FD&C Blue #2 Lake having a mean particle size of 20 microns. The lake particles were thoroughly dispersed in the paraffin and the dispersion was added slowly and with constant vigorous agitation to approximately 600 parts of water heated to a temperature of 180° F. After addition of the paraffin dispersion, the water was quickly cooled to 80° to 100° F. by addition of cold water. The solidified colored paraffin agglomerates were recovered from the water by straining the mixture through an 80 mesh screen. The agglomerates were then spread out on trays and air dried at room temperature. After drying the agglomerates were sifted through 35 mesh and 70 mesh screens. Those agglomerates which passed through the 35 mesh screen but not the 70 mesh screen were recovered for use as toothpaste speckles. The agglomerates had a Munsell Value of from 4 to 7 and a Munsell Chroma greater than 4.

Similar results are secured when bayberry wax is used in place of paraffin in the above process.

EXAMPLE III

Gel agglomerates of green urea-formaldehyde resin particles were prepared as follows:

15 gm. of agar and 60 gms of green urea-formaldehyde resin (same as Example I) were added to 325 ml distilled water at room temperature. The mixture was then heated to 180°-210° F. and mixed for about ten minutes. The resulting colored gel was spread in a thin layer on a drying tray and dried in an oven at 220° F. for 6 hours. The dried material was broken up into small pieces and pulverized to a powder. The powder was sifted as in Example II and colored gel agglomerates having a mean particle size within the range of 200 to 500 microns were recovered. The agglomerates had a Munsell Value between 4 and 7 and a Munsell Chroma greater than 4.

The urea-formaldehyde resin particles used in this example can be replaced with dyed cotton linters, dyed wood pulp, chromium oxide green, carbon black, FD&C Blue #2 dye lake or ultramarine pink particles of the same size with comparable results.

EXAMPLE IV

Gel agglomerates of chromium oxide green particles were prepared with a water-soluble polymer of acrylic acid cross linked with about 1% of a polyallyl ether of sucrose having an average of about 5.8 allyl groups for each sucrose molecule and sold under the tradename "Carbopol 940" by the B. F. Goodrich Chemical Company as follows:

15 gms of Carbopol 940 and 60 gms chromium oxide green (mean particle size 20 microns) were admixed in 400 ml. of distilled water at room temperature. The mixture was then heated to 180°-210° F. and agitated for about 10 minutes. The resulting colored gel was spread in a thin layer on a drying tray and dried in an oven at 220° F. for 6 hours. The dried material was broken up into small pieces which were then pulverized to a powder. The powder was sifted as in Example II and those gel agglomerates having a particle size within the range from 200 to 500 microns were recovered. These agglomerates had a Munsell Value between 4 and 7 and a Munsell Chroma greater than 4.

The chromium oxide green in the foregoing example can be replaced with colored melamine-urea-formaldehyde or phenol-formaldehyde resin, both as prepared in accordance with the Shaffer application cited hereinbefore, with comparable results.

EXAMPLE V

Cassava starch gel agglomerates of blue urea-formaldehyde resin particles were prepared by admixing 70 gms of cassava starch and 180 gms of blue urea-formaldehyde resin (particle size from 10 to 420 microns) in 400 ml of distilled water and forming agglomerates thereof in accordance with Examples III and IV. The agglomerates thus formed had a mean particle size of from about 200 to about 500 microns, a Munsell Value of from 4 to 7 and a Munsell Chroma greater than 4.

Toothpastes usually contain a cleaning and polishing agent, a humectant, a sudser, a binder, a sweetener, flavoring ingredients and water. The combination of such conventional components is referred to herein as the toothpaste base. Agglomerates prepared in accordance with the foregoing examples can be incorporated into toothpaste base at any point in the mixing of these components using conventional means.

Several toothpastes speckled with the agglomerates of this invention are shown in the following examples.

EXAMPLE VI

A toothpaste was prepared having the following composition:

| Component | % by Weight |
|---|---|
| Calcium pyrophosphate | 40.79 |
| Sorbitol (70% aqueous) | 20.39 |
| Glycerine | 10.19 |
| Sodium coconut monoglyceride sulfonate | 0.76 |
| Sodium carboxymethylcellulose | 1.20 |
| Sodium coconut alkyl sulfate (20% active) | 2.29 |
| Sodium fluoride | 0.22 |
| Sweeteners and flavor | 1.14 |
| Green urea-formaldehyde agglomerates* | .65 |
| Water | balance |

*Prepared in accordance with Example I

The toothpaste of this example had a distinctive green speckled appearance. The urea-formaldehyde agglomerates remained intact and color-fast through the mixing procedure and storage. When extruded from a toothpaste tube upon a toothbrush the paste maintained its speckled appearance but the agglomerates readily disintegrated when the paste was brushed upon the teeth and produced no unpleasant gritty feel in use.

Several additional toothpaste compositions were prepared which were identical in formulation to that of Example VI but containing the agglomerates set forth in Table 1 below in place of the green urea-formaldehyde agglomerates:

TABLE 1

| Example No. | Agglomerating Agent | Pigment | Preparation Method |
| --- | --- | --- | --- |
| VII | Arco Tuffin 30 | Urea-formaldehyde* | As in Example I |
| VIII | Carnauba wax | Chromium oxide green | As in Example I |
| IX | Carnauba wax | Dyed cotton linters | As in Example I |
| X | Carnauba wax | Dyed wood pulp | As in Example I |
| XI | Ceresin wax | Urea-formaldehyde* | As in Example I |
| XII | Agar-agar | Urea-formaldehyde | As in Example II |
| XIII | Cassava starch | Urea-formaldehyde | As in Example V |
| XIV | Avicel | FD&C Green #1 Lake | As in Example IV |

*Prepared in accordance with Example I of Shaffer application cited hereinbefore.

Each of the toothpastes of the foregoing examples had properties similar to those of Example VI except that the color of the speckling varied with the color of the particles.

What is claimed is:

1. A process for preparing agglomerates of pigment particles which comprises the steps of:
   (1) melting a wax having a hardness value of from 0 to 65;
   (2) uniformly dispersing water-insoluble, non-toxic, colorfast, pigment particles having a mean particle size within the range from about 5 to about 490 microns in the molten wax, said particles being selected from the group consisting of dyed thermosetting resin particles, chromium oxide pigments, carbon blacks, ultramarine blues, ultramarine pinks, ferric oxides, dyed cellulose particles and water insoluble dye lakes;
   (3) cooling the wax dispersion of pigment particles to solidification, said solidification yielding the final agglomerates or larger pieces; and
   (4) reducing the solid wax dispersion to agglomerates having a mean particle size within the range from about 200 to about 500 microns and a pigment particle concentration of from about 30% to about 50% by weight of the total agglomerates.

2. The process of claim 1 wherein the pigment particles have a mean particle size within the range of from about 10 to about 200 microns.

3. The process of claim 2 wherein the wax is selected from the group consisting of carnauba wax, candellila wax, montan wax, castor wax, ceresin wax, bayberry wax and paraffin.

4. The process of claim 2 wherein the pigment particles are substantially water-impervious, cross-linked, highly polymerized synthetic resin particles polymerized in an aqueous solution of a non-toxic water-soluble dye.

5. The process of claim 4 wherein the resin is a copolymer of urea and formaldehyde.

* * * * *